United States Patent [19]

Berg

[11] 4,001,678
[45] Jan. 4, 1977

[54] DISPLACEMENT METERING WITH INDEPENDENT ANCILLARY FLOW

[76] Inventor: Robert H. Berg, 196 Clinton Ave., Elmhurst, Ill. 60126

[22] Filed: June 16, 1975

[21] Appl. No.: 587,287

Related U.S. Application Data

[63] Continuation-in-part of Ser. No. 470,396, May 16, 1974, abandoned.

[52] U.S. Cl. .............................. 324/71 CP; 73/401; 137/240; 137/205
[51] Int. Cl.² ....................................... G01N 27/00
[58] Field of Search ............... 324/71 CP; 137/205, 137/392, 240; 73/401; 318/306

[56] References Cited

UNITED STATES PATENTS

| | | | |
|---|---|---|---|
| 2,712,624 | 7/1955 | Beattle | 318/306 |
| 3,523,546 | 8/1970 | Berg | 137/240 |
| 3,743,424 | 7/1973 | Coulter | 356/73 |
| 3,746,976 | 7/1973 | Hogg | 324/71 CP |
| 3,793,587 | 2/1974 | Thom et al. | 324/71 CP |
| 3,838,601 | 10/1974 | Dorman | 73/401 |

*Primary Examiner*—Robert Segal
*Assistant Examiner*—Vincent J. Sunderdick
*Attorney, Agent, or Firm*—Hill, Gross, Simpson, Van Santen, Steadman, Chiara & Simpson

[57] ABSTRACT

Displacement metering with two independently metered fluid flows comprises displacing fluid in laminar filament flow from a first chamber through a second chamber into a third chamber, the chambers being separated by a pair of spaced walls provided with coaxially aligned orifices in communicating series relationship. Flow in filamentary form is effected from the first chamber through the orifices seriatim into the third chamber, and flow is effected from the second chamber through the second orifice into the third chamber in sheathing relation to the filamentary flow. Differential pressure effects the flow from first to third chamber independently but concurrently with positive displacement effecting flow from the second chamber into the third chamber.

23 Claims, 6 Drawing Figures

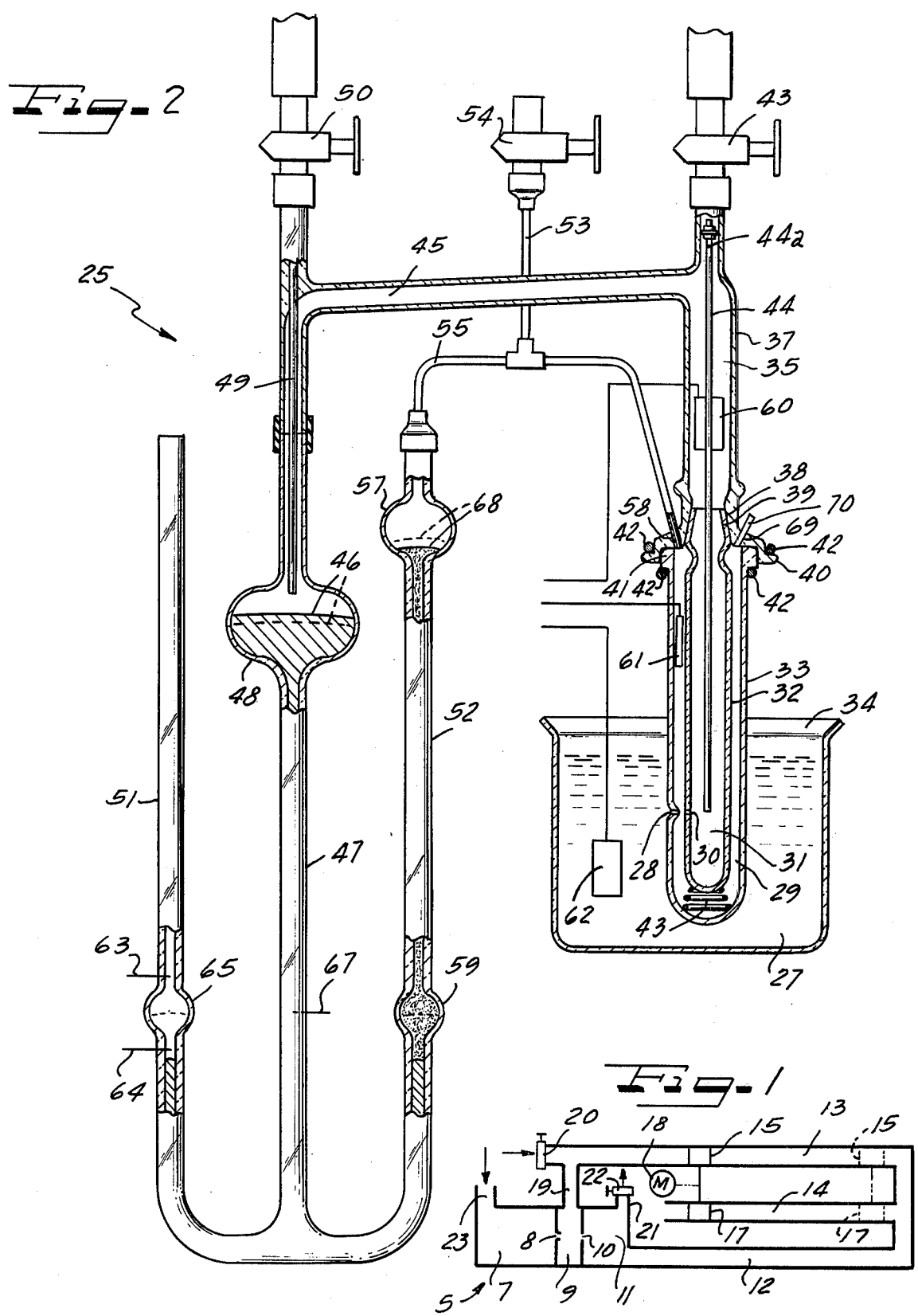

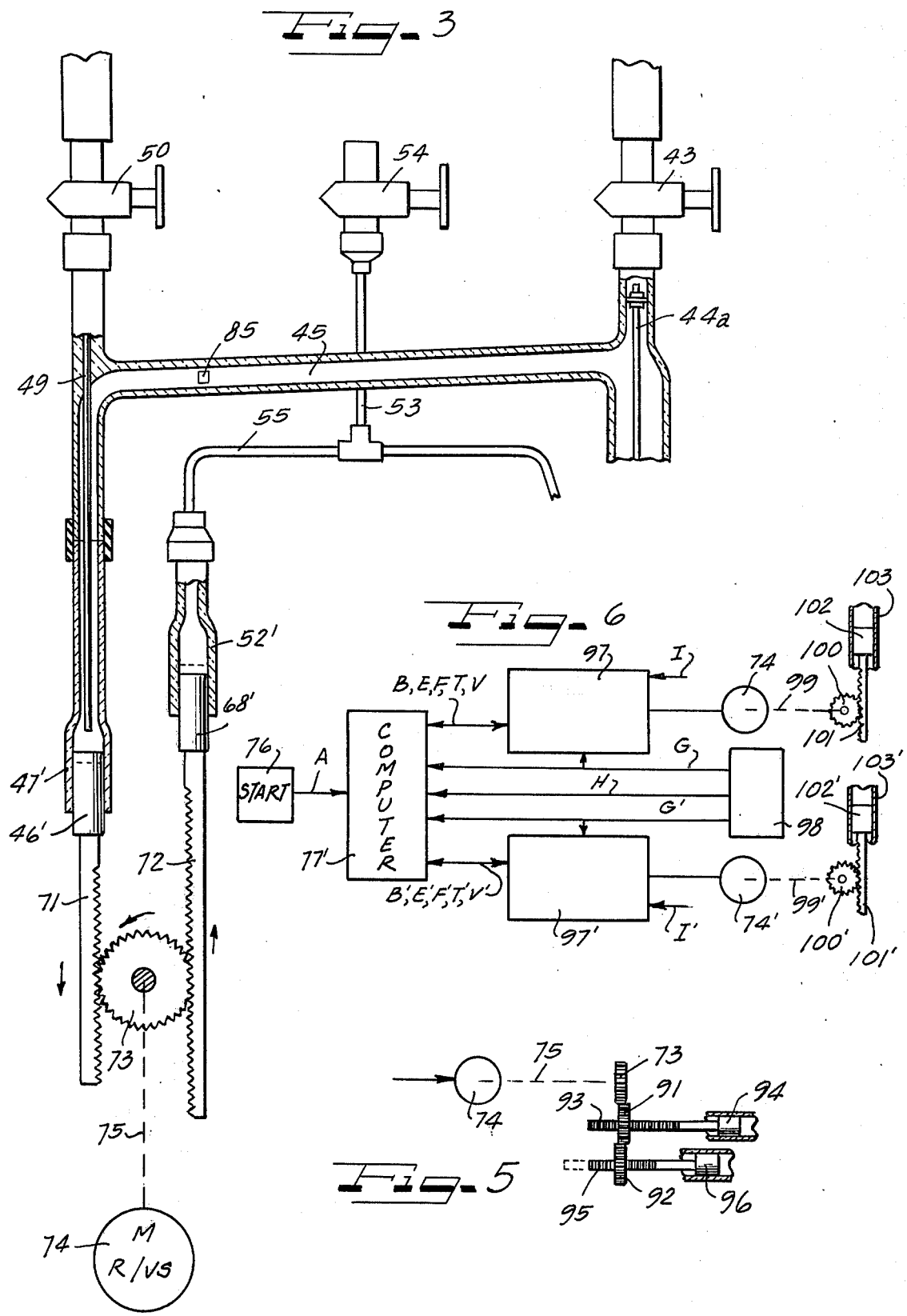

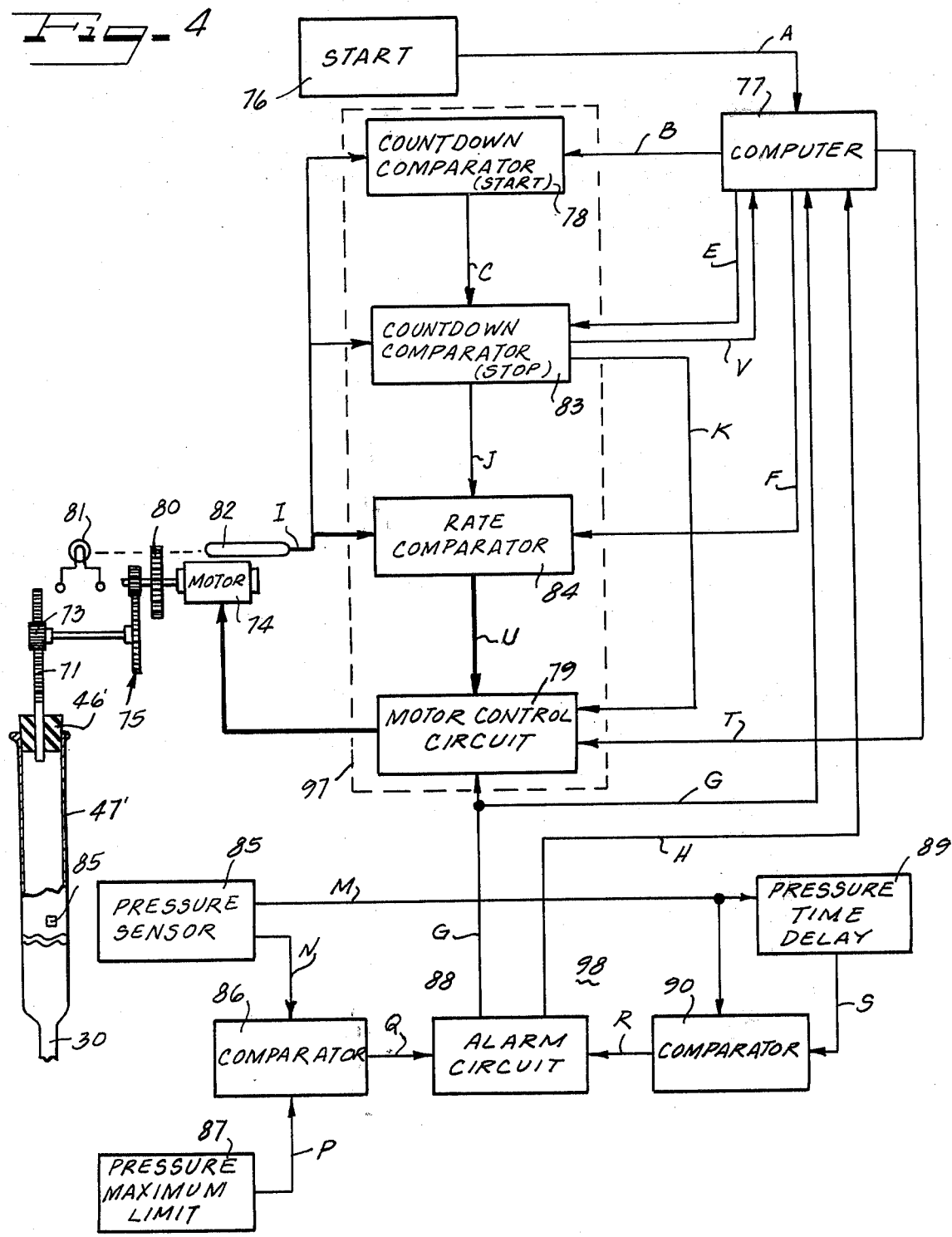

DISPLACEMENT METERING WITH INDEPENDENT ANCILLARY FLOW

This application is a continuation-in-part application based on my copending application of the same title, Ser. No. 470,396, now abandoned filed May 16, 1974.

This invention relates to displacement metering of fluid and is more particularly concerned with a new and improved method of and means for effecting two independently metered flows useful in so-called hydrodynamic focusing.

It has heretofore been proposed, for example in a paper by Spielman and Goren, "Journal of Colloid And Interface Science", Volume 26, pp. 175–182 (1968) to attain improved fidelity of particle size response in particle sensing or counting apparatus by so-called hydrodynamic focusing in a sensing orifice in one of a pair of tubes immersed in a bath of particle-free electrolyte, according to which a slight head of liquid in one of the tubes containing the suspension projects a small stream of the suspension into the electrolyte. Electrolyte is sucked through the sensing orifice in the other of the tubes, and the suspension-containing stream from the first tube is accelerated and thinned or narrowed so that the particles all travel essentially the same centralized streamline, for uniformity of approach and passage through the sensing aperture. The improvement has been later shown by others to be due to the virtual elimination of effects of anomalous electric field and hydraulic conditions at the rims and sidewalls of the sensing orifice. The attained increased fidelity of particle size response permits size analysis to be more precise and informative in the operation of a particle counter or particle sensing apparatus of the kind in which detection and measuring of particles in a fluid passing through an orifice is effected by modulation of an electrical current passing through or across the orifice. However, the arrangement proposed by Spielman and Goren has various shortcomings, not the least of which is that there is a considerable loss of precision due to lack of control over the sheathing of electrolyte.

It is therefore an important object of the present invention to provide a new and improved method of and means for providing two independently controlled coaxial flows, filamentary and sheathing, through a single orifice.

An other object of the invention is to provide a new and improved method of and means for attaining greater accuracy of proportions than between filamentary and sheathing flows with prior metering arrangements.

A further object of the invention is to provide a new and improved method of and means for hydrodynamic focusing while simultaneously maintaining accuracy in particle suspension metering and therefore particle concentration measurement.

Other objects, features, and advantages of the invention will be readily apparent from the following description of certain preferred embodiments thereof, taken in conjunction with the accompanying drawings although variations and modifications may be effected without departing from the spirit and scope of the novel concepts embodied in the disclosure, and in which:

FIG. 1 is a schematic illustration of apparatus for practicing the invention;

FIG. 2 is a schematic illustration of another embodiment of the invention especially suitable for use with particle sensing or counting instruments;

FIG. 3 is a schematic illustration of another embodiment of the invention, also suitable for use with particle sensing or counting instruments, and utilizing electric motor driven pumps;

FIG. 4 is a schematic illustration of a motor control and monitoring apparatus;

FIG. 5 is a schematic illustration of apparatus for controlling opposite linear displacement in two pumps by way of a single rotary input; and FIG. 6 is a schematic block diagram, similar to FIG. 4, illustrating motor control and monitoring apparatus for two independently operated, rack and pinion driven, pumps.

According to the present invention, displacement metering flow is effected by displacing fluid, such as liquid having entrained particles therein, in a filamentary stream into a low pressure chamber from another chamber through a pair of spaced orifices and through a sheathing fluid, i.e. liquid, in the space between the orifices. Positive displacement is effected on the fluid in the space to provide sheathing flow from the space in laminar relation to the filamentary flow as the fluid passes through the orifice which opens into the low pressure chamber.

In one system for practicing the invention, as exemplified in FIG. 1 displacement metering apparatus 5 providing for two independently metered flows has three orifice-connected chambers comprising a first chamber 7 connected by an orifice 8 with a second chamber 9 which, in turn, is connected by an orifice 10 with a third chamber 11. The orifices 8 and 10 are aligned, preferably coaxially, and spaced apart by the relatively narrow chamber 9. Leading from the chamber 11 is a passage 12 which has two parallel passage branches 13 and 14 provided with suitable unison coupled suction and pressure source means such as respective ganged pumping plug pistons 15 and 17 adapted to be actuated reciprocally in the passages 13 and 14 by suitable motor or actuating means 18 which may be manually, hydraulically, pneumatically, electrically or mechanically operated. While the passage branch 14 may be open to ambient pressure at its distal end, the passage 13 communicates through a branch duct 19 with the spacing chamber 9 providing a closed loop relationship of the chambers 9 and 11. On the opposite side of the branch 19 from the pump element 15 the branch 13 communicates with a suitable fluid source through a valve 20. Leading off from the chamber 11 is a take-off or discharge passage 21 controlled by a valve 22.

At the start of a metering operation involving the apparatus 5, the pump pistons 15 and 17 will be located in the branches 13 and 14 in a position which they assumed at the end of completion of a previous metering operating cycle, illustrated in full line as at the left hand end portion of the branch passage 14 and corresponding portion of the branch passage 13. At this time the valves 20 and 22 may be closed. Fluid such as liquid which may have entrained material, particulate or otherwise, to be metered is supplied into the chamber 7 through an inlet 23 under simple ambient pressure. Where the fluid entrains a particulate material, suitable agitating means (not shown) may be provided in or in association with the chamber 7. Then, with the valves 20 and 22 open, the pump pistons 15 and 17 are actuated as by the actuator 18 to move toward the right until they have reached a desired terminal point such as indicated in dash line at the right in FIG. 1. Such action of the pump pistons 15 and 17 draws liquid past the valve 20 into the branch passage 13, and discharges liquid from the chamber 11 through the outlet duct 21 past the open valve 22 by pump pressure of the piston 15 and 17 reflected through the passage 12. The valves 20 and 22 are then closed and the pump pistons 15 and 17 are actuated to move toward the left as viewed in FIG. 1. This causes displacement of fluid by suction generated by the piston pump 17 by way of the passage 12 in the chamber 11 and causes flow of fluid from the chamber 7 through the orifice 8 and in filamentry relation through fluid in the chamber 9 and through the orifice 10 into the chamber 11. Simultaneously and independently, fluid is displaced by pressure action of the pump piston 15 from the passage 13 through the connecting duct passage 19 into the chamber 9 and effects a laminar sheathing about the streamline of the filamentary flow from the chamber 7 through the orifices 9 and 10 with an improved focusing effect through the orifice 10 into the chamber 11. The ratio of displacement effected by the pump pistons 15 and 17 can be readily precalculated and determined for desired results. High degree of accuracy in volume of metered fluid through the orifice 10 and increased resolution with respect to the material transported from the chamber 7 through the orifice 7 is attained.

Having reference to FIG. 2, displacement metering apparatus 25 with independent ancillary flow is depicted adapted to glassware metering system, such as disclosed in my prior U.S. Pat. 3,523,546, especially suitable for use with a sensing apparatus such as a particle counter where accurate sample metering is essential. In such an arrangement, a first chamber 27 for containing the sample of particle entraining liquid electrolyte may be provided by a customary beaker or equivalent container 27a. Communication from the chamber 27 is by way of an orifice 28 at a suitable height above the bottom of the chamber 27 into a second chamber 29 which communicates through an orifice 30 aligned with the orifice 28 with a third chamber 31. In the illustrated example, the chambers 29 and 31 are provided by a double walled test tube arrangement comprising an inner test tube 32 and an outer orifice wall provided by a test tube 33 which may be formed in an integral one piece arrangement, but are preferably two separate telescopically related test tubes or hollow parts to facilitate cleaning. In any event, the test tubes 32 and 33 are disposed with walls in spaced relation. At its upper end, the chamber 27 has an inlet opening 34 through which ample material, such as liquid and entrained particles, is poured into the beaker chamber 27.

Although the orifices 28 and 30 are shown in horizontal alignment, which in practical construction facilitates usage of an orifice observation microscope, they may be located in other orientations, for example in the bottom of their respective tubes, where gravity effects on the particles would not tend to cause misalignment in particle trajectories.

Leading upwardly from the test tube chamber 31 is a passage 35 provided by a vertical member 37 supported in any suitable manner above the container 27a and to the lower end portion of which the test tubes 32 and 33 are secured, preferably detachably for cleaning purposes. For example, the lower end of the member 37 may have a bell mouth 38 into which complementally shaped head 39 of the inner test tube 32 fits tightly. Support for the outer test tube 33 is provided by an annular socket flange 40 on the lower end of the member 37 in which is received an upper beaded end 41 on the tube 32 and retained as by means of releasable clip structure 42. A spring 43 compressed between the bottoms of the test tubes 32 and 33 thrusts the inner tube 32 positively upwardly to assure tight fit at all times of the head 39 in the mouth 38.

At its upper end, the passage member 37 has a valve 43 which controls connection of the passage 35 and the chamber 31 with a suitable vacuum source by way of a small diameter vertical suction tube 44 having its lower end generally aligned with the orifice 30 to facilitate drawing off of the particle bearing stream, thereby reducing the chance of interference from particles that have already traversed the sensing zone orifice 30. Leading off from the chamber member 37, adjacently below the vacuum control valve 43, is a branch duct 45 leading to a body of mercury 46 in a vertical mercury column 47 having a bulbous upper mercury chamber reservoir enlargement 48 and with which a small flushing fluid nozzle tube 49 may communicate under control of a normally closed valve 50. At its lower end the columm 47 is connected with, respectively, a vertical tubular metering displacement column leg 51 at one side and a vertical sheathing flow displacement column 52 at the opposite side. Although the column leg 51 is, as is customary with this type of apparatus, open to atmosphere at its upper end, the column leg 52 is in communication with a sheathing fluid supply passage line 53 under the control of a valve 54. Connected with the supply line 53 in a line 55 extending from a bulbous chamber reservoir enlargement 57 at the upper end of the column leg 52 to a passage hole 58 leading through the flange 40 into the chamber 29. The lines 53 and 55 may be made from suitable ungiving plastic tubing such as so called Teflon spaghetti suitably coupled to the glassware, i.e. to the reservoir enlargement bulb 57 and the flange 40, and to the valve 54. The reservoir enlargement 57 is preferably slightly higher than the chamber 48 and sufficiently larger than a volumetric enlargement 59 in the lower portion of the column 52 so that the enlargement 57 will readily contain total fuid displacement from the lowest to the highest mercury position in the column 52.

The connecting joints and sleeves of the system are constructed to be unyielding to pressure differences as high as desired in use and the entire internal system of passageways is liquid filled such that virtually incompressible liquid continuity is established. A pinhole 44a in the upper end of the tube 44 provides release for any entrapped air.

The apparatus 25 is especially useful in association with particle sensing analyzing counting instruments of the kind available under the trademarks "Electro-Zone" and "Celloscope" from Particle Data, Inc., Elmhurst, Illinois, and which operate on the principle of passing a sample of electrolyte with entrained particles through an orifice providing a properly constricted path for an electrical current. Sensing of particles flowing through the orifice is effected by modulation of the electrical current by particles, such modulation being amplified and suitably recorded, totalized, visually observed on an oscilloscope, and the like. To this end, an electrode 60 is located in operative relation to the chamber 31 such as in the adjacent portion of the passage 35, an electrode 61 is located in the chamber 29 to be effective at the opposite end of the orifice 30 and alternatively or in addition an electrode 62 is located in the chamber 27 in operative relation to that end of the orifice 28. This provides for connection with the appropriate instrumentalities of the associate instrument. In addition, volumetric sensing electrodes 63 and 64 extend into the tubular passage of the leg column 51 above and below, respectively, a volumetric bulb 65. A grounding probe electrode 67 is in contact with the mercury in the column 47. The volumetric enlargement 59 may have whatever size relationship to the volumetric enlargement 65 may be necessary to provide a desired flow proportion of the sheathing flow to the filamentary flow.

In an operating cycle of the apparatus 25, opening of the vacuum control valve 42 will cause drawing up of the mercury 46 in the column 47 at a desired vacuum pressure, such as 150 mm Hg below atmospheric pressure. Concurrently, the valve 54 is opened to liquid source so that as the mercury in the column 47 rises and the mercury in the column 52 descends the supplied liquid is received in the reservoir enlargement 57. In order to isolate the electrical system components in the sampling side of the system from the mercury side of the system, an incompressible dielectric insulating medium 68 such as silicone oil which is not miscible with the liquid is permanently loaded into the column 52 above the mercury and in such volume as to avoid spilling over from the reservoir 57 into the line 55 in operation of the apparatus. Upon closing the valves 43 and 54, gravity displacement dropping of the mercury 46 in the column 47, represented by the height difference between the full line and dash line positions in the chamber 48, acting as suction pump piston means will cause filamentary stream flow of the sample material from the chamber 27 through the metering orifice 28 and through the chamber 29 and then through the metering orifice 30 into the chamber 32. Concurrently, rising of the mercury in the column 52 will act as force pump piston means in the closed loop system with the chambers 29 and 31 to drive fluid from the reservoir 57 and through the line 55 to effect force or pressure displacement of the sheathing fluid from the chamber 29 in laminar relation to the filamentary stream through the orifice 30. In the closed loop system, the mercury column means provide a device for automatically regulating and maintaining the pressure in the chamber 29 at a value intermediate an amibient pressure in the chamber 27 and the suction in the chamber 31. To assure freedom from air in the chamber 29, a bleed hole 69 is provided in the flange 40 through which any trapped air can be purged by pulling a normally closing cribbage-peg-like plug 70. It will be understood, of course, that the particle containing liquid in the sample chamber 27 and the sheathing liquid in the chamber 29 may be miscible electrolytes and the particles of a different electro-responsive nature such as nonconducting. As the particles pass through the orifice 30 they will modulate the electrical current between the electrodes 60 and 61, 62 and thus supply meaningful signals to the associated instrumentalities. By using the apparatus 25, accuracy is maintained in particle suspension metering and therefore particle concentration measurement while simultaneously effecting controlled hydrodynamic focusing sheathing flow.

Turning now to FIG. 3, the mercury piston pumps in FIG. 2 have been replaced by an electrically operated motor driven system comprising a tube 47' in which a piston 46' is slidably mounted, and a tube 52' in which a piston 68' is slidably mounted. The piston 46' is carried at one end of a rack 71 and the piston 68' is carried at one end of a rack 72. The racks 71 and 72 are simultaneously driven by a pinion 73 which is connected to an electric motor 74 by way of a mechanical linkage 75, such as a gear train or the like. It is readily apparent that as the pinion 73 is rotated counterclockwise, the rack 71 and piston 46' move downwardly and the rack 72 and the piston 68' move upwardly, which corresponds to the operating mode of the mercury pumps in FIG. 2.

The valves 43, 50 and 54 are employed for fluid delivery, flushing and the like, as in the previous embodiment, however the operating pressures are created by the pumps consituted by the tubes 47' and 52' and their respective pistons 46' and 68', rather than the mercury manometer type pumps illustrated in FIG. 2 and discussed above.

In order to provide accurately controlled filamentary and sheathing flows, the movement of the pistons 46' and 68' must be accurately controlled in such a manner that the measuring instrumentalities are provided with data during constant flow conditions. Therefore, the starting inertia of the prime mover system must be taken into account. Also, the speed of the motor must be maintained constant during the particle measurement process. In addition, care must be taken to prevent damage to the equipment upon the occurrence of abnormally great pressure differences and abnormal pressure changes. A system for controlling and monitoring the operation of the apparatus illustrated in FIG. 3 is illustrated in FIG. 4.

Turning to FIG. 4, the tube 47' and piston 46' have been illustrated on the left-hand side of the drawing as being driven by a rack 71, pinion 73 and electric motor 74 through the intermediary of a gear train 75. Attention is invited that the gear train 75 includes a gear 80 which is not connected in a driving relationship with any other gear. The purpose of the gear 80 is to report motor rotation, and thus piston displacement to the control and monitoring circuit.

At the beginning of a metering operation an operator initiates a start signal on a line A from a start circuit 76 which may be a simple switch. The start signal causes a computer 77 to issue a plurality of signals to control the operation of the motor 74.

The computer 77, includes a plurality of digital devices, as explained in greater detail hereinbelow with respect to particular control elements, and in the most simple case, may include a series of lights and operator control switches or signal controlled switches for causing the generation and transmission of serial or parallel data signals.

A first of the signals produced by the computer is applied by way of a line T to a motor control circuit 79 as a turn on signal for an amplifier, for example, which, in turn, provides a dc signal of a magnitude corresponding to desired motor speed. The motor begins to rotate and overcome the system inertia in attaining the desired motor speed.

In order to provide a predetermined measurement interval and to provide constant flows during such interval the inertia of the system may be accounted for and the flows may be controlled by simple digital techniques.

Inasmuch as a time delay is necessary, because of system inertia, before an actual measurement is initiated, the computer 77 issues digital signals, either serially or in parallel, representing a desired delay to set a counter in a countdown comparator 78. A settable or preset outpulser may be employed for this purpose to provide a serial input. A settable or preset register may provide the same data in parallel form as a start set point.

A light source 81 directs a light beam through the teeth of the rotating gear 80 to a photo detector 82 which generates pulses on a line I which is connected to countdown the counter of the countdown comparator 78 to zero. Upon reaching zero, the countdown comparator 78 issues a signal on the line C to indicate that the motor should have attained the desired speed to perform a measurement operation.

The start signal on the line C may be employed to enable the countdown comparator 83 by closing an electronic switch in the comparator 83 to permit entry of the pulses on the line I.

The computer also issues, either serially or in parallel, digital signals over a line E to a countdown comparator 83 to set a counter to a count which indicates that point at which a measurement operation should stop. Again, an outpulser or a register may provide the stop set point data to the countdown comparator 83. The pulses on the line I are fed into the countdown comparator 83 to exercise the counter therein toward zero. Upon reaching zero, the countdown comparator issues a stop signal on a line J and a stop signal to the computer 77 on the line K to cause the computer to turn off the motor via the line T.

It is readily apparent that the signals issued on the lines C and J may take the place of the probes 63 and 64 in FIG. 2 to indicate starting and stopping of metering to a measuring instrumentality. The countdown comparator may also issue the stop signal, or a similar signal, by way of a line V to the computer 77 to indicate completion of the measuring process. The line V, for example, may be connected to an electronic switch for turning off the energized circuits of the computer. The stop signal on the line J may also be employed to operate an electronic switch in the rate comparator 84 discussed below to stop a rate comparison. This signal may also be used to reverse the motor, via appropriate switches, and reset the apparatus.

The system has thus far provided for a start-up delay and an operating interval. However, due to a variety of changing conditions, such as wear, friction, voltage variations, etc., the actual speed of the motor may vary from the desired speed. Therefore, means are provided for automatically adjusting the speed of the motor.

The photo detector 82, the motor control circuit 79 and the computer 77 are connected to a rate comparator 84 and a dynamic control loop is established as indicated by the heavier lines connecting the motor control circuits 79, the motor 74, the photo detector 82 the rate comparator 84 and back to the motor control circuit 79. As mentioned above, the computer provides a signal on the line T which is of a magnitude, or causes the amplifier in the motor control circuit 79 to provide a signal of a magnitude such that the motor 74 will operate at the desired speed. The computer 77 also provides a signal on the line F to a first RC circuit in the rate comparator 84. The resultant storage in the capacitor of the RC circuit is proportional to the desired speed signal on the line T, or issuing from the motor control circuit 79. The photo detector 82 is also connected to an RC circuit in the rate comparator 84 and the capacitor of this RC circuit is therefore pulsed to store energy representing the actual speed of the motor 74. The two RC circuits are connected to an operational amplifier which has an output which is connected by way of a line U to the motor control circuit 79. The line U is connected as a control input for varying the magnitude of the output of the aforementioned amplifier in the motor control circuit 79 and the operational amplifier in the rate comparator 84 provides a control signal for adjusting the output of the amplifier in the motor control circuit up and down to compensate for a difference in actual motor speed and desired motor speed. The dynamic control loop therefore prevents overshoot and hunting at the start of a measurement operation and provides constant filamentary and sheathing flows during measurement.

Inasmuch as the chambers and conduits may include and be generally defined by fragile components, such as glass tubes, a pressure monitoring system is active during the entire process. In FIG. 4 the pressure monitoring system has been generally referenced 98 and is illustrated as comprising a pressure sensor 85, a comparator 86, a pressure maximum limit reference circuit 87, an alarm circuit 88, a pressure time delay 89 and a comparator 90.

Advantageously, the pressure sensor 85 may be a piezoelectric type pressure sensor and may be mounted in the tube 45 so as to sense the negative pressure provided by the pump 46', 47' on the side of the orifice 30 (FIG. 1) which is common to both pumps. The orifice 30 has been schematically illustrated as a constriction in the tube 47' in FIG. 4 and the pressure sensor 85 has been illustrated in FIG. 4 within the tube 47' in that the same communicates with and experiences the same pressure as the tube 45. The pressure sensor 85 provides a signal by way of a line end to a comparator 86 which receives a reference signal by way of a line P from a pressure maximum limit circuit 87. The comparator 86 may be constituted, therefore, by a simple differential circuit, such as a biased amplifier, a differential amplifier, operational amplifier or the like which responds to provide an output signal on a line Q in response to a pressure signal which is greater than the maximum pressure limit indicated by the reference signal on the line P. The comparator 86 is connected to an alarm circuit which may be constituted by an electronic switch which is responsive to the signal on the line Q to place an alarm signal on a line G. The alarm signal on the line G may be ORed with the stop signal on the line K to turn off the motor. Additionally, the alarm signal on the line G is fed to the computer to indicate a maximum pressure condition, by a lamp or the like, and to cause switching off, either automatically or manually, of the motor control circuits.

The pressure sensor also sense an actual pressure signal by way of a line M to the pressure time delay circuit 99, which may include a delay line having a delay of a fraction of a second up to several seconds depending on the particular operational system, after which the delay signal is fed by way of a line S to the comparator 90. The pressure signal of the line M is also fed to the comparator 90 so that actual pressure is compared with a delayed preceding pressure condition. The comparator 90 may be constituted by an amplifier, such as a differential amplifier, which will respond to a predetermined difference in the two pressure signals to provide a corresponding signal to the alarm circuit 88 by way of a line R. The alarm circuit 88 may also include an electronic switch which is responsive to the signal R to transmit a pressure difference alarm signal to the computer by way of a line H. The signal on the line H may be employed as the signal on the line G to operate an indicating device and/or turn off the system. In the event that the computer receives an alarm signal on the line G or on the line H, either signal may operate an electronic switch to provide a stop signal to the motor control circuit by removing the signal applied to the line T and/or to reverse the motor to relieve pressure by removing blockages or the like.

Referring to FIG. 5, a variation of the structure for simultaneously moving the pistons in opposite directions is illustrated for the motor 74. The motor 74 is connected by way of a gear train 75 to a pinion 73. The pinion 73 is meshed in driving engagement with a gear 91 which, in turn, is meshed in driving engagement with a gear 92. The gears 73, 91 and 92 are mounted for rotation, however they are prevented from axial movement. Each of the gears 91 and 92 includes an axial threaded bore which receives a respective lead screw 93 and 95 therethrough. A pair of pistons 94 and 96 are mounted on the lead screws 93 and 95, respectively. A similar construction could utilize a pair of gears, driven by the pinion 93, and fixed for mutual rotation with respective lead screws. In this case, each lead screw would carry a threaded nut arrangement which, in turn, would be connected to a respective piston.

In FIG. 4, the countdown comparators 78,83, the rate comparator 84 and the motor control circuit 79 constitute a motor control for the motor 74. If it is desired to move the pistons by way of separate motors, the circuit of FIG. 4, with the exception of the start circuit and the pressure monitoring system are basically doubled. FIG. 6 shows such a system.

In FIG. 6, a motor control 97 is illustrated as being connected to a motor 74 as in FIG. 4. The motor 74 in FIG. 6 is, however, mechanically linked to a piston 102 within a tube 103 by way of a gear train 99, a pinion 100 and a rack 101. Similarly, a motor 74' is connected to a piston 102' within a tube 103' by way of a gear train 99', a pinion 100' and a rack 101'. The motor 74 is driven by a motor control 97' and each of the motor controls 97 and 97' are similarly connected to a computer 77' and a pressure monitoring system 98. It is readily apparent that most of the signals and signal lines are provided in duplicate. The only difference between the two systems is the provision of the desired speed signals from the respective motor control circuits (79) in that different motors may be utilized or different motor speeds of the same type of motor may be utilized in moving the respective pistons.

The filamentary flow, sheathing flow, and combined flow may be designated A, B, and C respectively. Now, although the foregoing describes systems for controlling flows B and C, and thus by positive displacement difference flow A, similar systems may readily be devised, by one skilled in the art, to control A and C, with B following, or to control A and B, with C following.

Although I have described my invention by reference to particular illustrative embodiments thereof, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim as my invention:

1. Displacement metering apparatus with two independently metered flows, especially adapted for use with a particle sensing instrument, comprising:

first, second and third fluid chambers;

coaxially aligned orifices in communicating series relationship comprising a first orifice connecting said first and second chambers and a second orifice connecting said second and third chambers;

means for effecting and metering filamentary flow from said first chamber seriatim through said orifices into said third chamber;

means for concurrently effecting and metering flow from said second chamber in sheathing laminar relation to said filamentary fluid flow and through said second orifice into said third chamber, said means for effecting filamentary flow comprising a first tube connecting a communication with said third chamber and a first piston slidably mounted in said first tube;

said means for effecting a sheathing flow comprising a second tube connecting a communication with said second chamber and a second piston slidably mounted in said second tube; and electric motor means connected to and concurrently operating said first and second pistons, said electric motor means comprising an electric motor, and including a motor control connected to said electric motor, said motor control comprising first means for energizing said electric motor to operate at a desired speed, second means for sensing a predetermined number of revolutions of said motor and generating a start signal for the particle sensing apparatus, third means for sensing a second predetermined number of revolutions after the start signal to generate a stop signal for the particle sensing apparatus, and fourth means connected to said first means for comparing actual motor speed with respect to the desired speed and causing said first means to adjust the energization of the motor.

2. Displacement metering apparatus with two independently metered flows, especially adapted for use with a particle sensing instrument, comprising:

first, second and third fluid chambers;

coaxially aligned orifices in communicating series relationship comprising a first orifice connecting said first and second chambers and a second orifice connecting said second and third chambers;

means for effecting and metering filamentary flow from said first chamber seriatim through said orifices into said third chamber;

means for concurrently effecting and metering flow from said second chamber in sheathing laminar relation to said filamentary fluid flow and through said second orifice into said third chamber, said means for effecting filamentary flow comprising a first tube connecting a communication with said third chamber and a first piston slidably mounted in said first tube, said means for effecting a sheathing flow comprising a second tube connecting a communication with said second chamber and a second piston slidably mounted in said second tube; and electric motor means connected to and concurrently operating said first and second pistons, said first and second tubes including frangible material, and comprising pressure sensing means in one of said tubes for sensing the pressure therein, and shut off means connected to said pressure sensing means for causing deenergization of said electric motor means in response to a pressure greater than a predetermined limit.

3. Apparatus according to claim 2, comprising alarm means connected to and operated by said shut off means.

4. Apparatus according to claim 2, comprising pressure change detecting means connected to said pressure sensing means and to said shut off means for causing operation of said shut off means in response to detection of changes in pressure which are greater than a predetermined amount.

5. In particle analysis apparatus of the type in which first, second and third fluid chambers are connected in fluid communication via interposed first and second orifices, and in which a filamentary first fluid flow is effected from the first chamber through the second chamber and into the third chamber, and a second fluid flow is effected from the second chamber into the third chamber in a sheathing laminar relation to the first flow to establish a total flow which is the sum of the first and second fluid flows, the improvement therein comprising:

flow control means for simultaneously and independently metering two of the three specified fluid flows so that each of said first and second fluid flows is a fixed fraction of said third fluid flow.

6. The improved apparatus of claim 5, including fixed walls between said chambers having said orifices therethrough in aligned space relation.

7. The improved apparatus of claim 5, wherein said flow control means comprises means for applying a suction to said third chamber to cause said first flow through said first and second orifices.

8. The improved apparatus of claim 5, wherein said flow control means comprises means for applying a pressure in said second chamber which is greater than the pressure in said third chamber to cause said sheathing second flow.

9. The improved apparatus of claim 5, wherein said flow control means comprises a suction connected to said third chamber and a device for automatically regulating and maintaining a pressure in said second chamber at a value intermediate an ambient pressure in said first chamber and the suction in said third chamber.

10. The improved apparatus of claim 5, wherein said flow control means comprises a mercury piston device for effecting both the first and second fluid flows.

11. The improved apparatus of claim 5, wherein said flow control means comprises a closed loop system including two of the three specified chambers.

12. The improved apparatus of claim 11, wherein said closed loop system comprises the second and third chambers.

13. The improved apparatus of claim 5, wherein said flow control means comprises a first tube connected in communication with said third chamber, a first piston slidably mounted in said first tube, a second tube connected in communication with said second chamber, a second piston slidably mounted in said second tube, and electric motor means connected to and concurrently operating said first and second pistons.

14. The improved apparatus of claim 13, wherein said electric motor means comprises a single motor mechanically linked to both of said first and second pistons.

15. The improved apparatus of claim 13, wherein said electric motor means comprises first and second electric motors connected to respective ones of said first and second pistons, and electric control means connected to said first and second motors for operating said motors in a predetermined speed relationship.

16. In a method of analyzing particles in which a filamentary fluid flow is effected from a first chamber through a first orifice, a second chamber and a second orifice into a third chamber, and a second fuid flow is effected from the second chamber through the second orifice into the third chamber in a sheathing laminar relation to the first flow to establish a total flow which is the sum of the first and second fluid flows, the improvement therein comprising:

simultaneously and independently metering two of the three specified fluid flows so that each of the first and second fluid flows is a fixed fraction of the third fluid flow.

17. The improved method of claim 16 comprising the step of applying a suction to the third chamber to effect the filamentary flow.

18. The improved method of claim 16, comprising the step of applying a pressure to the second chamber relative the third chamber to displace fluid fron the second chamber in sheathing laminar relation to the filamentary fluid flow.

19. The improved method of claim 16, comprising the steps of applying a suction to the third chamber to cause the filamentary fluid flow and regulating and maintaining a pressure in the second chamber at a value intermediate an ambient pressure in the first chamber and the suction in the third chamber to effect the sheathing laminar fluid flow.

20. The improved method of claim 16, further defined by the step of operating a mercury piston device to establish pressure differentials from the first chamber to the second chamber to the third chamber to effect both the filamentary metering and fluid flow and the sheathing laminar metering and fluid flow.

21. The improved method of claim 16, further defined by concurrently metering and flowing fluid through a closed loop including the second and third chambers.

22. The improved method of claim 16, comprising the steps of operating an electric motor connected to a pair of pistons to effect both the filamentary and sheathing flows, and controlling the speed of the electric motor to provide constant flows during a predetermined period.

23. The improved method of claim 16, comprising the steps of operating a pair of electric motors connected to a pair of pistons, respectively, to effect the filamentary and sheathing flows, respectively, and controlling the speeds of the electric motors to provide constant flows during a predetermined period.

* * * * *